United States Patent
Yahata et al.

(10) Patent No.: US 7,082,189 B2
(45) Date of Patent: Jul. 25, 2006

(54) X-RAY DISTRIBUTION ADJUSTING FILTER APPARATUS AND X-RAY CT APPARATUS USING THE SAME

(75) Inventors: Mitsuru Yahata, Tokyo (JP); Akira Izuhara, Tokyo (JP); Masashi Maida, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 34 days.

(21) Appl. No.: 10/891,979

(22) Filed: Jul. 14, 2004

(65) Prior Publication Data
US 2005/0013411 A1    Jan. 20, 2005

(30) Foreign Application Priority Data
Jul. 15, 2003 (JP) .............. 2003-197029

(51) Int. Cl.
G21K 3/00 (2006.01)
(52) U.S. Cl. .............. 378/156; 378/158; 378/159
(58) Field of Classification Search ........ 378/156–159, 378/65
See application file for complete search history.

(56) References Cited
U.S. PATENT DOCUMENTS

| | | | |
|---|---|---|---|
| 3,717,768 A | 2/1973 | Edholm et al. | |
| 4,288,695 A | 9/1981 | Walters et al. | |
| 5,148,465 A * | 9/1992 | Mulder et al. | 378/156 |
| 5,881,127 A | 3/1999 | Molloi et al. | |
| 6,307,918 B1 | 10/2001 | Toth et al. | |
| 6,325,539 B1 | 12/2001 | Bromberg et al. | |
| 6,501,828 B1 | 12/2002 | Popescu | |
| 6,529,575 B1 | 3/2003 | Hsieh | |
| 6,618,466 B1 | 9/2003 | Ning | |
| 6,647,095 B1 | 11/2003 | Hsieh | |

FOREIGN PATENT DOCUMENTS
JP    2002-102217    4/2002

* cited by examiner

Primary Examiner—Edward J. Glick
Assistant Examiner—Jurie Yun
(74) Attorney, Agent, or Firm—Carl B. Horton, Esq.; Armstrong Teasdale LLP

(57) ABSTRACT

An X-ray distribution adjusting filter apparatus for supplying a desired X-ray intensity distribution or adjusting the X-ray distribution to a desired profile, the bowtie filter as the X-ray distribution adjusting filter apparatus has a fixed section having a base portion and inclined portions, first and second movable sections configured to be tiltable pivoting on a center point, and first and second deformable sections whose cavities defined by the fixed section, the movable sections and an expansible bellows is to be filled with fluid, wherein the inclined faces of the fixed section and the flat faces of the movable sections are caused to approach or move away from each other by the tilting of the movable sections pivoting on the center point to vary the quantity of the fluid in the cavities of the movable sections, and to vary the sectional shape of the X-ray absorbing portion of the bowtie filter.

18 Claims, 11 Drawing Sheets

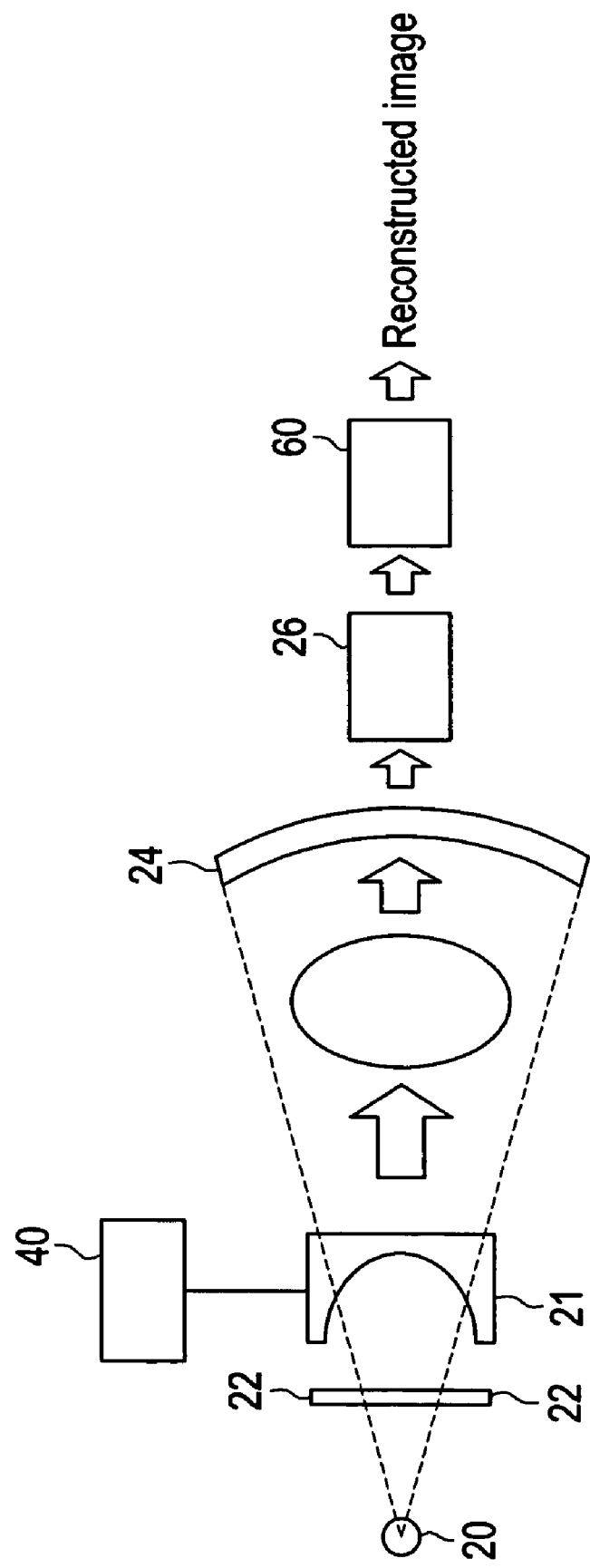

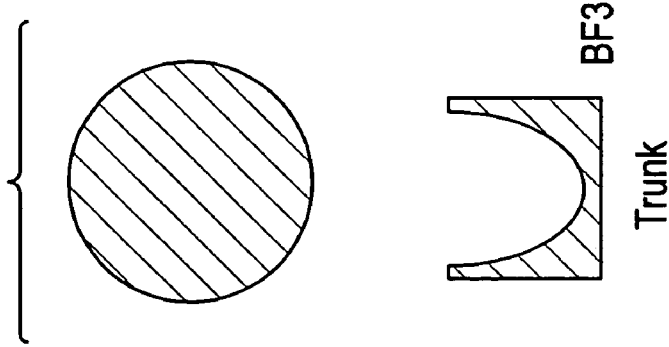
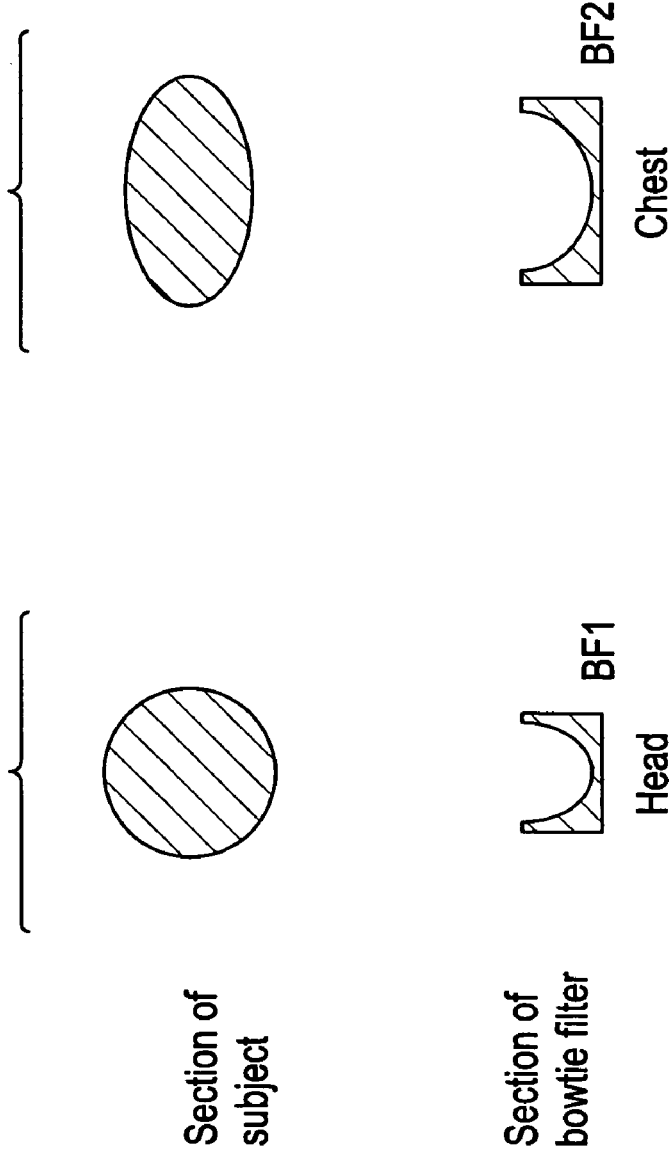

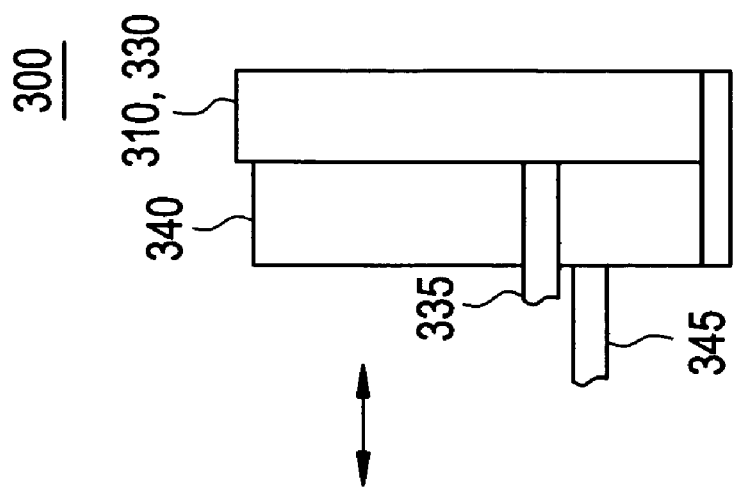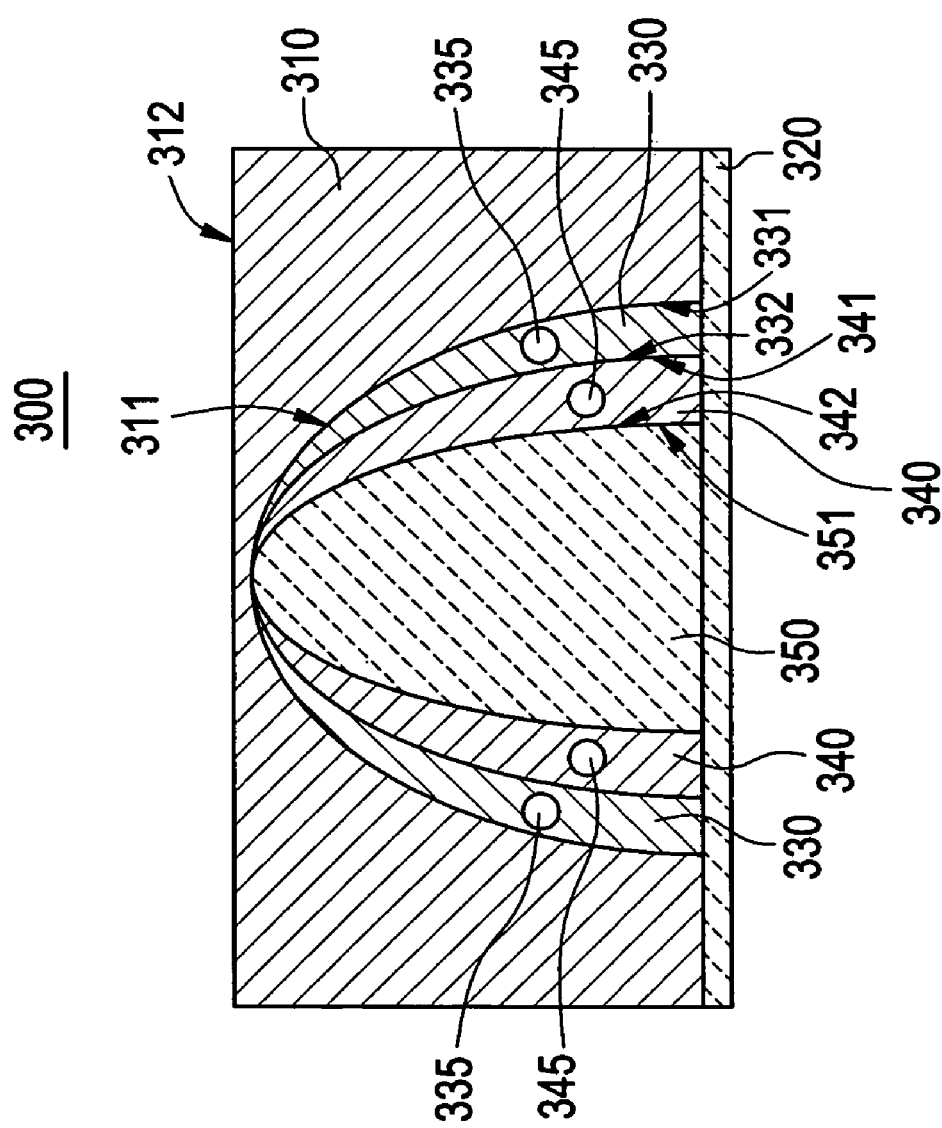

X-RAY DISTRIBUTION ADJUSTING FILTER APPARATUS AND X-RAY CT APPARATUS USING THE SAME

CROSS REFERENCE TO RELATED APPLICATION

This application claims the benefit of Japanese Application No. 2003-197029 filed Jul. 15, 2003.

BACKGROUND OF THE INVENTION

The present invention relates to an X-ray CT apparatus and an X-ray distribution adjusting filter apparatus, known as a bowtie filter, for use in X-ray CT apparatus.

An X-ray source used in an X-ray CT apparatus outputs X-rays having a certain energy width. The linear absorption coefficient of X-rays penetrating the subject is dependent on the X-ray energy, and there is manifested a beam hardening (BH) effect, which means that the greater the penetration length of the subject, the higher the average energy tends to be. Therefore, the penetration intensity of X-rays, i.e. the value of projected information to generate signals detected by an X-ray detector in the X-ray CT apparatus, is not in proportion, but in a nonlinear relationship, to the penetration length.

Since the BH effect invites the cupping effect of inviting a drop in intensity in the central part of the reconstructed image on an X-ray CT apparatus, the detection signals from the X-ray detector have to be corrected, and this correction is accomplished by figuring out for each channel of the X-ray detector a correction coefficient for the value of projected information to generate a reconstructed image of uniform intensity.

For correction at a higher level of accuracy, a phantom is used. As such a phantom, a cylindrical phantom whose plurality of sections have different diameters large enough to cover substantially the whole field of view (FOV), arranged at the center of the image, is picked up, and projected information from these sections of the phantom is used to increase the accuracy of correction using the correction coefficient.

For such X-rays which diffuse (disperse) as they deviate from the center axis between the X-ray source and the X-ray detector, in order to uniformize the intensity of X-rays penetrating the subject (or the phantom) or to adjust the profile of the X-rays, the X-ray emitting section of the X-ray source is provided with an X-ray distribution adjusting filter apparatus, known as a bowtie filter, and the X-ray intensity is thereby made as uniform as possible independent of the distance from the center axis.

[Patent Reference 1]
Japanese Patent Application Laid-open No. 2002-102217

However, the sectional shape of the subject region positioned in the FOV may greatly differ from one subject to another. For instance, even of the same subject, the sectional shape greatly differs among the head, chest and trunk of the body. Of course, adults and children entirely differ in overall sectional shape.

Therefore, even though the X-ray intensity distribution is adjusted by using an X-ray distribution adjusting filter apparatus, known as a bowtie filter, appropriate adjustment is further desired to take account of the difference in the overall size of the subject and differences among regions of the same subject.

Especially in recent years, even more precise tomography with an X-ray CT apparatus has come to be required, and appropriate adjustment of X-ray distribution differentiated according to the examined (imaged) region of the subject is needed along with accurate channel-by-channel correction of projected information value using the aforementioned phantom.

SUMMARY OF THE INVENTION

Therefore, an object of the present invention is to provide an X-ray distribution adjusting filter apparatus capable of providing a desired X-ray intensity distribution or adjusting the X-ray distribution to a desired profile.

The invention is also intended to provide an X-ray CT apparatus capable of highly precise imaging by using such an X-ray distribution adjusting filter apparatus.

According to a first aspect of the invention, there is provided an X-ray distribution adjusting filter apparatus having, in order to adjust distribution of penetration intensity of X-rays emitted from an X-ray source and expanding in a predetermined shape outward from the center axis of the X-rays, a curved face having a predetermined curvature along the center axis, and including an X-ray absorbing portion formed of an X-ray absorbing material, wherein the distribution of the penetration intensity of X-rays is adjusted by varying the shape of the X-ray absorbing portion of the X-ray distribution adjusting filter apparatus.

Preferably, the X-ray distribution adjusting filter apparatus should have a fixed section having a base portion uniform in thickness along the center axis and inclined portions linked to or formed integrally with the base portion, symmetrically formed about the center axis and on both sides of the center axis, and each having an inclined face with a predetermined inclination relative to a flat face of the base portion; first and second movable sections formed on both sides of the center axis, each configured to pass the center axis and to be tiltable on a plane orthogonal to the center axis, pivoting on a center point, which is the position where one-side ends of the inclined faces of the fixed section are coupled, and having a flat face positioned on the side opposite to the inclined faces of the fixed section and a curved face opposite to the flat face; and first and second deformable sections having opposite ends each opposite to the coupling position of each of the inclined faces of the fixed section, and expansible means disposed between the ends of the flat faces of the first and second movable sections, opposite to the opposite ends, and expanding or contracting according to the pivoting of the first and second movable sections, in which cavities defined by the inclined faces of the fixed section, the flat faces of the movable sections and the expansible means are filled with fluid to keep the insides of the cavities in a filled state, wherein the fixed section and the movable sections are formed of an X-ray absorbing material to constitute the X-ray absorbing portion, and the inclined faces of the fixed section and the flat faces of the movable sections are caused to approach or move away from each other by the tilting of the first and second movable sections pivoting on the center point to vary the quantity of the fluid in the cavities of the movable sections, and to vary the sectional shape of the X-ray absorbing portion of the X-ray distribution adjustment filter apparatus.

Also preferably, the X-ray distribution adjusting filter apparatus should have a basic X-ray distribution adjusting filter portion symmetrically shaped about the center axis and having a curved inner wall, and a removable X-ray distribution adjusting filter portion symmetrically shaped about the center axis and having a first curved outer wall whose shape is identical with the shape of the curved inner wall of the basic X-ray distribution adjusting filter portion and a first curved inner wall on a face opposite to the first curved outer wall, capable of being inserted to or discharged from an inside of the basic X-ray distribution adjusting filter portion, with the first curved outer wall being run along the curved inner wall of the basic X-ray distribution adjusting filter portion, wherein the basic X-ray distribution adjusting filter portion and the removable X-ray distribution adjusting filter portion are formed of a material that can absorb X-rays, and the insertion or removal of the removable X-ray distribution adjusting filter portion into or from the basic X-ray distribution adjusting filter portion causes the sectional shape of the X-ray absorbing portion of the X-ray distribution adjusting filter apparatus to vary.

According a second aspect of the invention, there is provided an X-ray CT apparatus comprising: an X-ray source; X-ray detecting means; and an X-ray distribution adjusting filter apparatus having, in order to adjust the distribution of the penetration intensity of X-rays emitted from the X-ray source and dispersing in a predetermined shape from the center axis of the X-rays linking the focal position of the X-ray source and the center of the X-ray detecting means on a plane orthogonal to the center axis, a curved face along the center axis, and including an X-ray absorbing portion formed of an X-ray absorbing material, in which the distribution of the penetration intensity of said X-rays can be adjusted by varying the sectional shape of the X-ray absorbing portion of the X-ray distribution adjusting filter apparatus.

As the bowtie filter mentioned above, one or another can be selected out of the variety described above.

According to a third aspect of the invention, there is provided an X-ray CT apparatus comprising: an X-ray source; X-ray detecting means; an X-ray distribution adjusting filter apparatus having, in order to adjust the distribution of the penetration intensity of X-rays emitted from the X-ray source and dispersing in a predetermined shape from the center axis of the X-rays linking the focal position of the X-ray source and the center of the X-ray detecting means on a plane orthogonal to the center axis, a curved face along the center axis, and including an X-ray absorbing portion formed of an X-ray absorbing material; and an X-ray distribution adjusting filter apparatus control section for adjusting the distribution of the penetration intensity of X-rays penetrating the X-ray absorbing portion by varying the position of the X-ray absorbing portion of the X-ray distribution adjusting filter apparatus relative to the focal position of the X-ray source.

As the bowtie filter mentioned above, one or another can be selected out of the variety described above.

The use of the X-ray distribution adjusting filter apparatus according to the invention makes it possible to obtain any desired X-ray intensity adjustment characteristic.

Also, the use of the X-ray distribution adjusting filter apparatus according to the invention in an X-ray CT apparatus makes it possible to obtain picked-up images of high precision.

Further objects and advantages of the present invention will be apparent from the following description of the preferred embodiments of the invention as illustrated in the accompanying drawings.

BRIEF DESCRIPTION OF THE DRAWINGS

FIG. 3 illustrates the concept of the X-ray CT apparatus illustrated in FIG. 1. and FIG. 2.

FIGS. 4(A) through 4(C) show examples of the shapes of the subject and the desired sectional shapes of bowtie filters (the X-ray absorbing portions).

FIG. 6 are configurational diagrams of the shape of a bowtie filter in a second mode of implementation for realizing the shapes and characteristics of the desired bowtie filters (the X-ray absorbing portions) examples of which are shown in FIGS. 4(A) through (C), wherein

FIG. 8 are configurational diagrams of the shape of a bowtie filter in a second mode of implementation for realizing the shapes and characteristics of the desired bowtie filters (the X-ray absorbing portions) examples of which are shown in FIGS. 4(A) through (C), wherein FIG. 8(A) shows a section view and FIG. 8(B), a profile.

DETAILED DESCRIPTION OF THE INVENTION

A preferred mode of implementing the invention to provide an X-ray CT apparatus and an X-ray distribution adjusting filter apparatus, known as a bowtie filter, for use in the X-ray CT apparatus will be described below with reference to the accompanying drawings.

The overall configuration of an X-ray CT apparatus 1 in this mode of implementation will be described with reference to FIG. 1 through FIG. 3.

Figure 1:
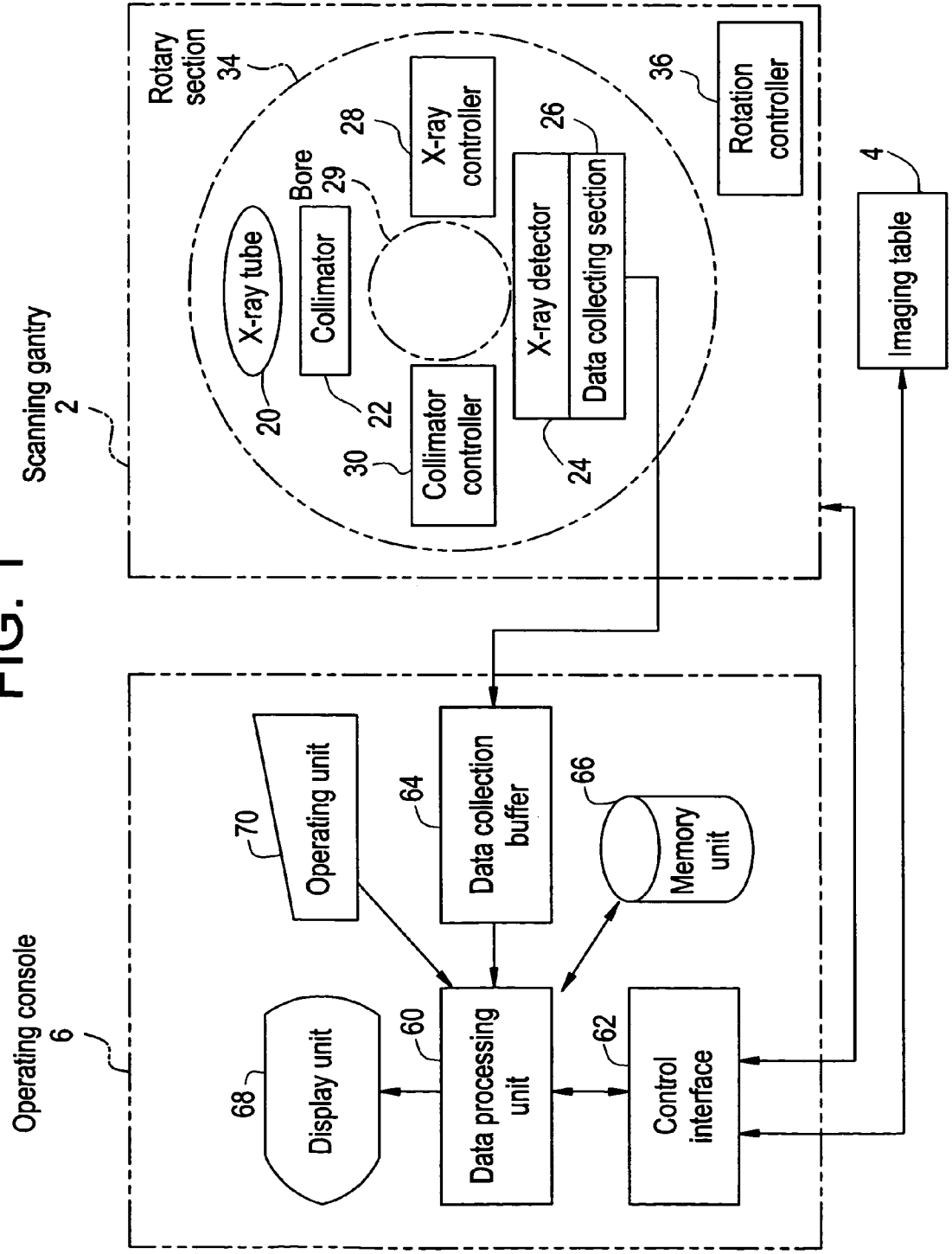
FIG. 1 is a block diagram showing the overall configuration of the X-ray CT apparatus as one mode of implementing the CT apparatus according to the invention.

FIG. 1 shows the overall configuration of the X-ray CT apparatus; FIG. 2, a partial sectional view of the X-ray CT apparatus illustrated in FIG. 1; and FIG. 3, a conceptual diagram of processing by the X-ray CT apparatus illustrated in FIG. 1.

The X-ray CT apparatus illustrated in FIG. 1 is provided with a scanning gantry 2, an imaging table 4 and an operating console 6.

Scanning Gantry

The scanning gantry 2 has a rotary section 34 and a rotation controller 36 for turning the rotary section 34.

Figure 2:
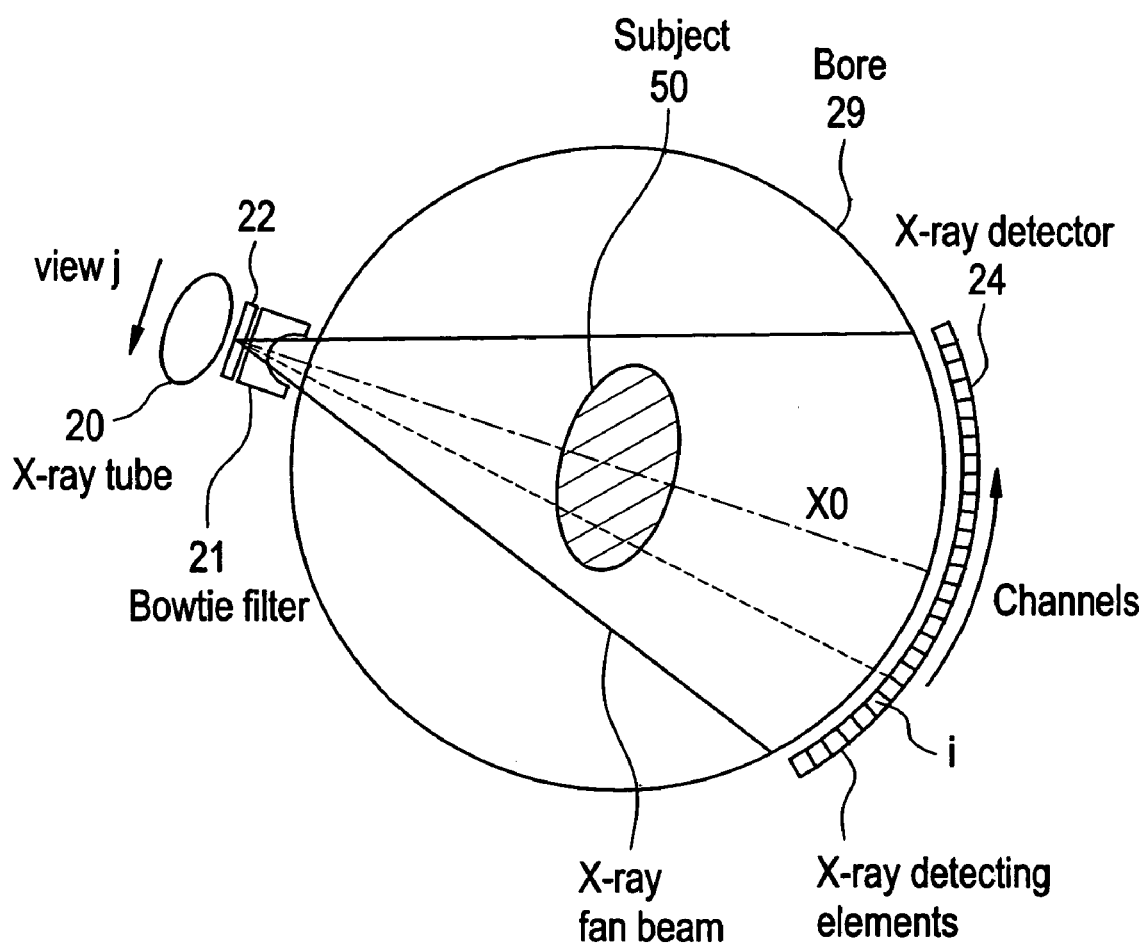
FIG. 2 shows the positional relationship among the X-ray tube, the X-ray detector and the X-ray distribution adjusting filter apparatus (bowtie filter) in the X-ray CT apparatus illustrated in FIG. 1.

In the rotary section 34 are disposed, as its section is illustrated in FIG. 2 in an enlarged view, an X-ray tube 20 and an X-ray detector 24 arranged opposite to each other via a bore 29. The rotary section 34 is further mounted with a bowtie filter 21 (FIG. 2 and FIG. 3), a collimator 22 (FIG. 2 and FIG. 3), a collimator controller 30, an X-ray controller 28 and a data collecting section 26. Incidentally, the relative positions of the bowtie filter 21 and the collimator 22 may be reversed. Also, the orientation of the concave face of the bowtie filter 21 may be reverse to what is illustrated.

When examination is to be done, a subject 50 is positioned in the bore 29, or when calibration is to be done, a phantom is positioned in the bore 29 (the description hereinafter will refer only to the subject 50). The subject 50 positioned is mounted on a cradle (not shown) in the bore 29 positioned at the center of the rotary section 34.

The X-ray tube 20 corresponds to the X-ray source according to the invention, and the X-ray detector 24 corresponds to the X-ray detecting means according to the invention.

Incidentally, although the mode in which the X-ray distribution adjusting filter apparatus is realized corresponds to the aforementioned bowtie filter 21, the term "X-ray distribution adjusting filter apparatus" will not be used, but the term "bowtie filter" will be used, in the following description of the mode of implementation in this specification for the sake of expedience.

The rotary section 34 rotates while being controlled by the rotation controller 36. In this rotation, X-rays are emitted from the X-ray tube 20 toward the X-ray detector 24, X-rays having penetrated the subject 50 are detected by the X-ray detector 24, and the data collecting section 26 collects the results of detection by the X-ray detector 24.

The results of detection are processed by the operating console 6 as projected information of each view.

The radiation of X-rays from the X-ray tube 20 is controlled by the X-ray controller 28. The X-rays radiated from the X-ray tube 20 are shaped by the collimator 22 to take on a predetermined shape (or profile), for instance a fan-shaped X-ray team, i.e. fan-beam X-rays. The collimator 22 is controlled by the collimator controller 30.

The bowtie filter 21 controls the intensity of X-rays expanding in a fan shape on both sides of a center axis $X_o$ connecting the focal position FP of the X-ray tube 20 and the center axis and directed toward the X-ray detector 24 to be equal over all the channels of the X-ray detector 24, and the X-rays come incident on the X-ray detector 24 via the bore 29.

For this reason, the bowtie filter 21 is formed of a material that absorbs X-rays, and has a concave face (or a curved face) having predetermined curvature defined according to the radiation distribution profile of the X-rays and the shape of the X-ray detector 24. Thus it has a curved face whose thickness is smaller in the part around the center axis $X_o$ and increases toward the periphery.

Details of the bowtie filter 21 and various other bowtie filters (X-ray distribution adjusting filter apparatus according to the invention) will be described afterwards.

For the adjustment of these bowtie filter 21 and various other bowtie filters (X-ray distribution adjusting filter apparatus according to the invention) to be described afterwards, there is provided a bowtie filter control section 40 (FIG. 3). Details of the bowtie filter control section 40 will also be described afterwards.

Incidentally, whereas the X-ray distribution adjusting filter apparatus in the present invention corresponds to the bowtie filter described in regard to the mode of implementation, the X-ray distribution adjusting filter apparatus control means corresponds to the bowtie filter control section 40.

To add, as stated above, the relative positions of the bowtie filter 21 and the collimator 22 may be reverse.

Also, the orientation of the concave face (curved face) of the bowtie filter 21 may be reverse to what is illustrated.

The X-ray detector 24, as illustrated in FIG. 2, has a plurality of channels of X-ray detection elements arranged in an array form in the directions of fan-beam X-ray expansion. In this way, the X-ray detector 24 is configured as a multi-channel detector in which a plurality of channels of X-ray detection elements are arranged in an array form, and it forms an overall shape having a cylindrically concave X-ray incident face. The X-ray detector 24 is configured of, for instance, a combination of scintillators and photodiodes. Incidentally, the X-ray detector 24 may consist of semiconductor X-ray detection elements using cadmium telluride (CdTe) or the like or ionization chamber type X-ray detection elements using Xc gas.

To the X-ray detector 24 is connected the data collecting section 26. The data collecting section 26 collects data detected by the individual X-ray detection elements of the X-ray detector 24.

Operating Console

The operating console 6 has a data processing unit 60, a control interface 62, a data collection buffer 64, a memory unit 66, a display unit 68 and an operating unit 70.

The data processing unit 60 is composed of, for instance, a computer having high data computing and processing functions. To the data processing unit 60 is connected the control interface 62.

To the control interface 62 is connected the imaging table 4 of the scanning gantry 2. The data processing unit 60 controls the scanning gantry 2 through the control interface 62. Thus, the data collecting section 26, the X-ray controller 28, the collimator controller 30 and the rotation controller 36 in the scanning gantry 2 are controlled by the data processing unit 60 through the control interface 62.

To the data processing unit 60 is connected the data collection buffer 64. To the data collection buffer 64 is connected the data collecting section 26 of the scanning gantry 2. Data collected by the data collecting section 26 are inputted to the data processing unit 60 through the data collection buffer 64.

The data processing unit 60 reconstructs an image by using penetrating X-ray signals, i.e. projected information, collected through the data collection buffer 64. To the data processing unit 60 is connected the memory unit 66. The memory unit 66 stores, among other items, projected information collected into the data collection buffer 64, reconstructed tomographic information, and a program for realizing the functions of the X-ray CT apparatus in this mode of implementation.

To the data processing unit 60 are connected the display unit 68 and the operating unit 70. The display unit 68 displays tomographic information and other items of information outputted from the data processing unit 60. The operating unit 70 is operated by an operator, and inputs various instructions and items of information to the data processing unit 60. The operator uses the display unit 68 and the operating unit 70 to interactively operate the X-ray CT apparatus in this mode of implementation.

Imaging Table

The imaging table 4, connected to the data processing unit 60 via the control interface 62, is mounted with various switches and operating instruments for operating the X-ray CT apparatus, and a display unit for displaying X-ray CT images processed by the operating console 6.

Preferable Shape of Bowtie Filter

As described above, X-rays radiated from the X-ray tube 20 pass a phantom which simulates a human body, and the intensity of the X-rays is so adjusted as to uniformize the intensity distribution over all the channels of the X-ray detector 24. It is preferable for the bowtie filter 21 as the X-ray distribution adjusting filter apparatus to have a shape which would allow appropriate adjustment of the distribution of X-rays emitted from the X-ray tube 20 according to the size of the subject 50, the region to be examined (region to be imaged), and the configuration of the region to be examined of the subject 50.

Thus, the shape of the bowtie filter is so designed that, wherever the X-rays may pass, (the thickness of the human body)+(the thickness of the bowtie filter) be constant.

For instance, as shown in FIGS. 4(A) through (C), it is preferable to replace the sectional shape of the bowtie filter 21, i.e. the concave shape and thickness of the X-ray absorbing portion having a concave shape, with what has the illustrated shape to match the substantially circular head whose overall size is smaller than that of the trunk (belly), the oval chest and the trunk (belly) whose overall size is larger than that of the head.

The mode of implementation in which the sectional shape (the concave shape and thickness) of the bowtie filter 21, i.e. the shape of the X-ray absorbing portion, is substantially varied will be described below.

First Mode of Implementation

Figure 5:
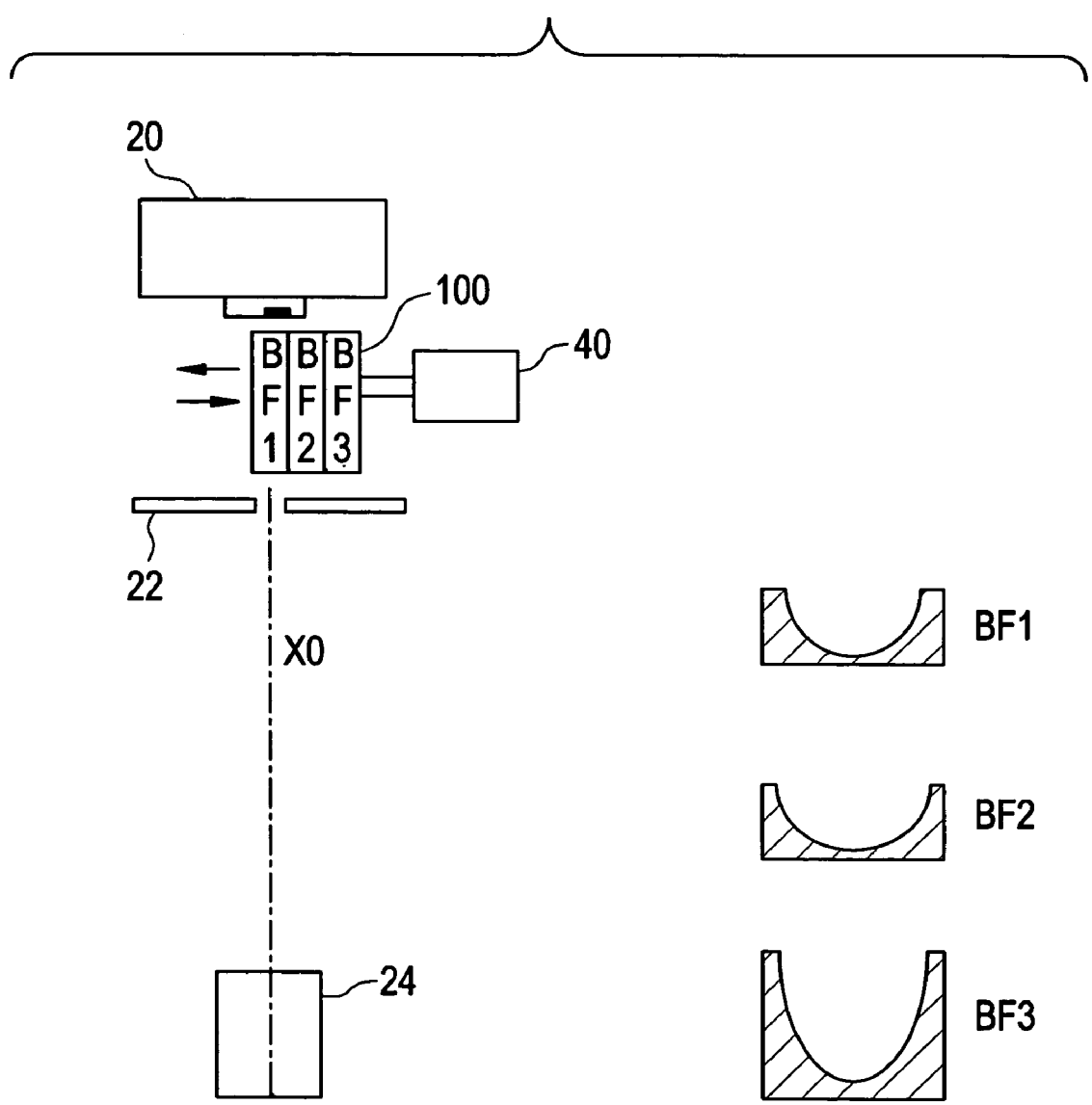
FIG. 5 is a partial schematic configurational diagram of the shape of a bowtie filter in a first mode of implementation for realizing the shapes and characteristics (the X-ray absorbing portions) of the desired bowtie filters examples of which are shown in FIGS. 4(A) through 4(C) and of an X-ray CT apparatus using it.

FIG. 5 shows a method of selecting the X-ray absorbing portion of the bowtie filter in a first mode of implementing the present invention by way of a sectional view of the section between the X-ray tube 20 and the X-ray detector 24 shown in FIG. 1.

Between the X-ray tube 20 and the collimator 22 there is positioned a bowtie filter 100 in the first mode of implementing the invention. The bowtie filter 100 as the X-ray distribution adjusting filter apparatus in the first mode of implementing the invention can be moved either manually or by a motor in the directions indicated by arrows.

The section of the bowtie filter 100 positioned between the X-ray tube 20 and the X-ray detector 24, i.e. the sectional shape of the X-ray absorbing portion, can be substantially varied, and the effect of X-ray distribution adjustment thereby varied, by linking in advance unit bowtie filters BF1 through BF3 having three different X-ray absorbing portions shown in FIGS. 4(A) through 4(C) and moving them in the directions of the arrows.

The orientation of the concave face (curved face) of the bowtie filter 100 can be reverse to what is illustrated in FIG. 4 and FIG. 5.

Although the bowtie filter 100 illustrated in FIG. 5 represents, by way of example, a case in which it consists of only three different X-ray absorbing portions constituting the combination of bowtie filters BF1 through BF3, the number of bowtie filters to be combined and the sectional shape and size of each bowtie filter can be selected to appropriately match the state of the subject.

In the first mode of implementation described with reference to FIG. 5, adjustment can be made of the X-ray intensity distribution from the X-ray tube 20 to the X-ray detector 24 in the direction vertical to the sheet of FIG. 5 around the center axis $X_o$. Preferably, as illustrated in FIG. 2, the light reception intensities of all the channels of the X-ray detector 24 from one of its ends to the other with the central part of the X-ray detector 24 interposed therebetween can be made substantially uniform.

By using the bowtie filter 100 in the first mode of implementation, it is possible not only to image the subject 50 but also to calibrate each channel of the X-ray detector 24 by performing beam hardening with-a phantom, to image the subject 50 on the basis of the result of that calibration, collect image data into the data collecting section 26, generate a reconstructed image with the data processing unit 60 and thereby obtain an X-ray CT image of high precision.

Second Mode of Implementation

FIGS. 6 show the configuration of a bowtie filter 200 as the X-ray distribution adjusting filter apparatus in a second mode of implementing the present invention.

Figure 6A:
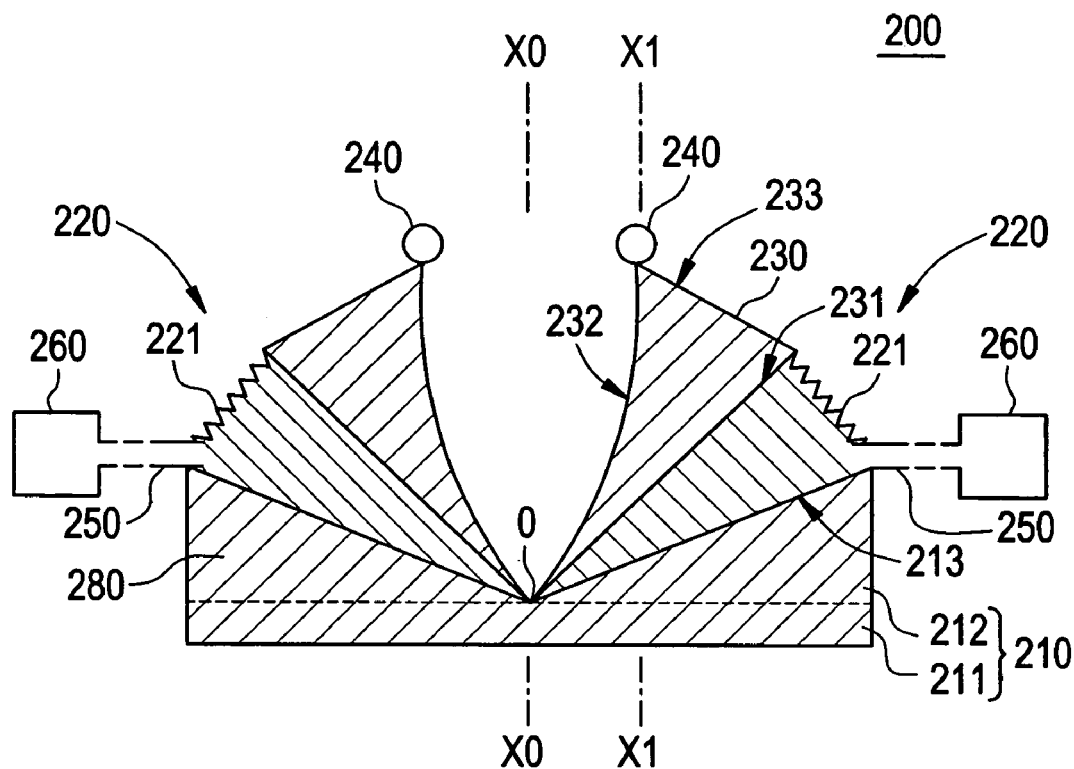
FIG. 6(A) shows a section view and FIG. 6(B), a profile.
Figure 6B:
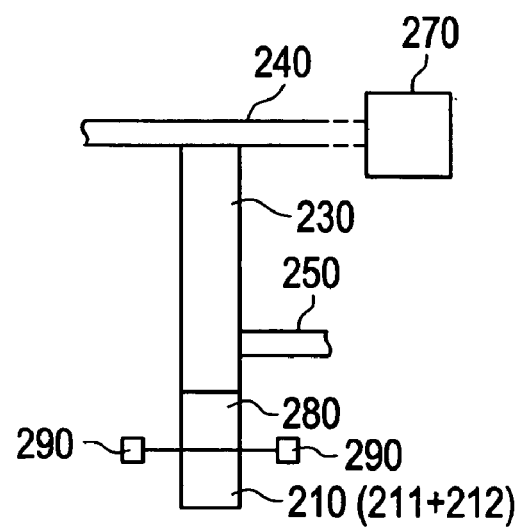

FIG. 6(A) shows a sectional view of the bowtie filter 200 in the second mode of implementing the invention, and FIG. 6(B), a sectional profile of the same along line X1—X1 in FIG. 6(A).

The bowtie filter 200 illustrated in FIGS. 6(A) and 6(B) is configured to be laterally symmetric about the center axis $X_o$ passing the center point O, and has a fixed section 210, deformable sections 220, movable sections 230 and movable axes 240.

Although the right and left movable sections 230 and deformable sections 220 need not be symmetric, a case in which they are laterally symmetric is shown with respect to this mode of implementation as a preferable example.

The fixed section 210 has a base portion 211 and inclined portions 212. The base portion 211 and the inclined portions 212 may either be formed as separate parts linked to each other in the position indicated by the broken line or be integrally formed from the outset.

The fixed section 210, as the X-ray absorbing portion (filter) for absorbing X-rays, is formed of an X-ray absorbing material, such as carbon powder or aluminum.

The inclined portions 212 on the both sides have inclined faces 213 having a laterally symmetric shape about the center axis $X_o$. The angle of the inclined faces 213 with respect to the flat face of the fixed section 210 is represented by α.

The position of the center axis $X_o$ where the inclined portions 212 on the both sides are coupled is called the center point O. The center point O corresponds to the part at the center of the fixed section 210 where its thickness is the smallest, or the position where the two inclined faces 213 on the two sides of the fixed section 210, having a symmetric shape to be described afterwards, are coupled. The movable sections 230 are configured to be movable pivoting on this center point O.

When the bowtie filter 200 is to be positioned between the X-ray tube 20 and the X-ray detector 24, it is so positioned that the center point O and the center axis $X_o$ illustrated in FIG. 6(A) and the center axis $X_o$ illustrated in FIG. 2 meet each other.

Each of the movable sections 230 has a shape defined by a flat face 231, a curved face 232 and an end face 233. The curved face 232 is formed as a standard curved face resulting from the rearrangement and unification of the concave faces (the curved faces) of the various bowtie filters (the X-ray absorbing portions) shown in FIGS. 4(A) through 4(C).

The movable sections 230 are X-ray absorbing portions formed of the same or similar X-ray absorbing material as the fixed section 210.

The movable sections 230 have laterally symmetric shapes about the center axis $X_o$, and each of the two movable sections 230, independent of the other, is fixed to the fixed section 210 to be tiltable around the center point O of the fixed section 210.

To add, in order to prevent the quantity of penetrating X-rays from being varied and the distribution characteristics of the X-rays from being distorted by their penetration of the fixed portions of the movable sections 230 fixed to be tiltable around the center point O of the fixed section 210, it is preferable for the centers of tilting of the movable sections 230 to be fixed, as illustrated in FIG. 6(B), with fixing members 290 on the outside where the X-rays of the bowtie filter 200 penetrate.

Each of the deformable sections 220 has expansible means, for instance an expansible bellows 221, fixed between the external end (the other end than the aforementioned coupling position) of the inclined face 213 of the fixed section 210 and the flat face 231 of the movable section 230, and a cavity defined by the inclined face 213, the flat face 231 and the bellows 221 is filled with fluid with low viscosity (or liquid) 280 having low X-ray absorption characteristics. As such fluid 280 can be used, for instance, carbon fluid dissolved in carbon liquid.

Since part of the expansible bellows 221 does not transmit X-rays, no consideration X-ray transmissibility needs to be considered in selecting the material of the bellows 221, and any expansible and durable material can be used for the bellows 221. As such a material, elastic rubber can be used for example.

As the expansible means for use in the present invention is not limited to the bellows 221, but may simply be something like a bag than can expand and contract. Thus, as the expansible means for use in the invention, anything can be selected from various alternatives only if it expands when the aforementioned cavity is filled with fluid 280, contracts when the fluid 280 is discharged from the cavity and does not obstruct the operation of the movable section 230 to be described afterwards.

The bowtie filter 200 further has pipes 250, a fluid accommodating section 260 and movable means 270 for moving the movable axes 240. Incidentally, the pipes 250, the fluid accommodating section 260 and the movable means 270 may be included in the X-ray CT apparatus instead of in the bowtie filter 200. In this mode of implementation, however, the bowtie filter apparatus is treated as what includes the pipes 250, the fluid accommodating section 260 and the movable means 270.

Although the fluid accommodating section 260 is illustrated in two positions in FIG. 6(A), it is actually one unit common on both sides.

The movable means 270 can be either a manual mechanism or a mechanical one using a motor, screws and the like if only it can tilt the movable sections 230 via the movable axes 240. Where automatic control to be described afterwards is to be done, an automatically controllable mechanical mechanism shall be used as the movable means 270.

The deformable sections 220 are linked to the fluid accommodating section 260 via the pipes 250. The fluid accommodating section 260 applies a predetermined pressure to the fluid 280 having low X-ray absorption characteristics to keep the pressure in the cavities of the deformable sections 220 constant.

The movable sections 230 are tilted around the center point O as the movable axes 240 are rotated by the movable means 270, and the flat faces 231 of the movable sections 230 approach or move away from the inclined face 213 of the fixed section 210.

Such an approach of the flat faces 231 of the movable sections 230 to, or their moving away from, the inclined face 213 of the fixed section 210 causes the bellows 221 to expand or contract, and the volumes of the cavities of the deformable sections 220 vary.

When the volumes of the cavities of the deformable sections 220 become smaller, the fluid 280 in the cavities is squeezed out to flow into the fluid accommodating sections 260 via the pipes 250. Conversely when the volumes of the cavities of the deformable sections 220 become greater, the fluid 280 under a predetermined pressure in the fluid accommodating sections 260 flows into the cavities of the deformable sections 220 via the pipes 250 and fill the cavities.

The fluid accommodating sections 260 do not obstruct the movability of the aforementioned movable sections 230, but presses the fluid 280 so that the fluid 280 appropriately fill the cavities of the deformable sections 220 in compliance with the movable sections 230.

Figure 7A:
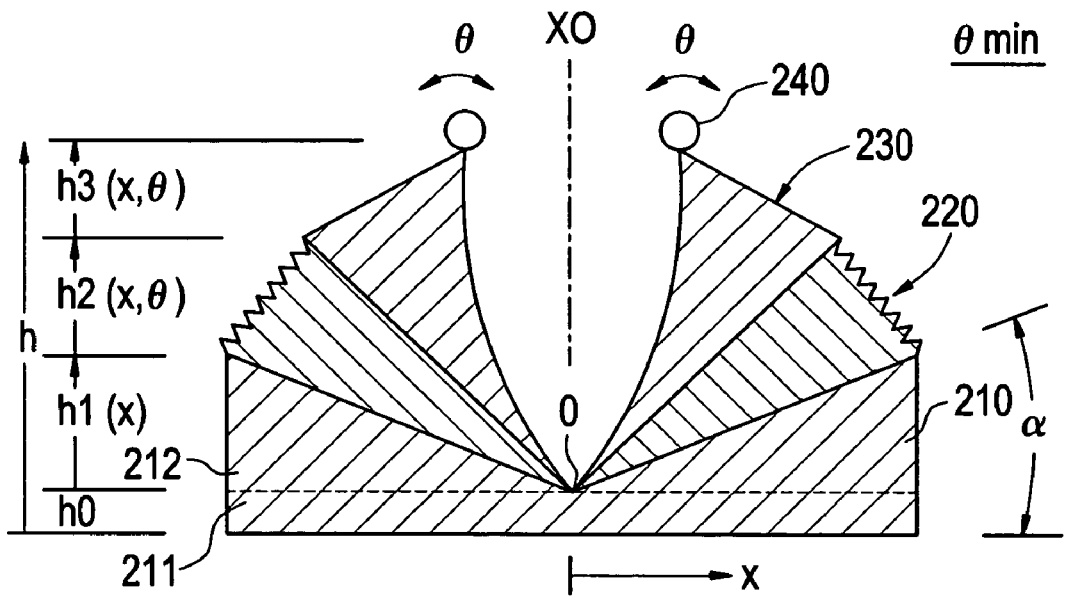
FIGS. 7(A) and 7(B) are sectional diagrams illustrating the manner of operation of the bowtie filter in the first mode of implementation illustrated in FIG. 6(A).
Figure 7B:
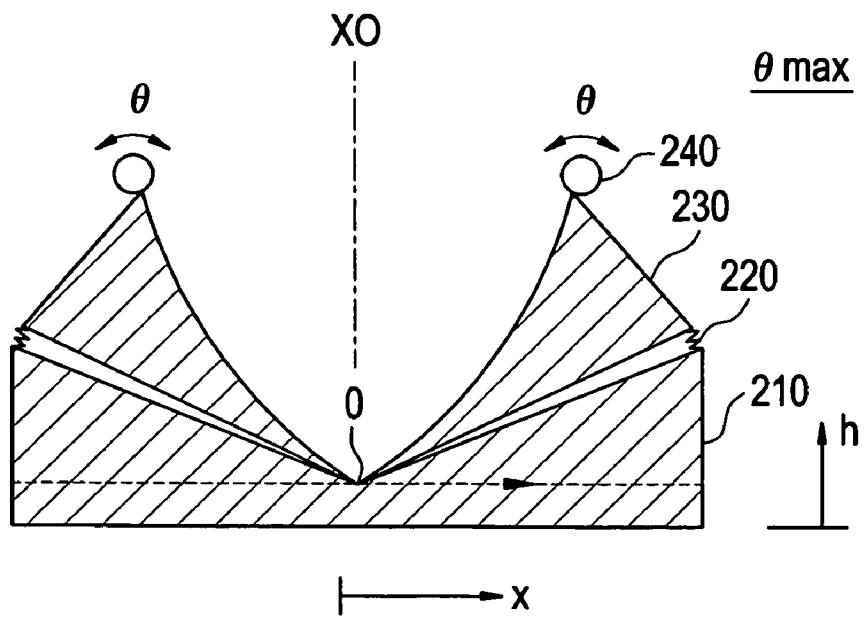

FIGS. 7(A) and 7(B) show an example of manner in which the bowtie filter 200 operates.

FIG. 7(A) shows a state in which the movable sections 230 on the two sides of the bowtie filter 200 are narrowed to the minimum, while FIG. 7(B) shows a state in which the movable sections 230 on the two sides of the bowtie filter 200 are expanded to the maximum.

In the state illustrated in FIG. 7(A), the cavities of the deformable sections is filled with the fluid 280, and the thickness h (or height or depth) of the bowtie filter 200 in the x direction, which is orthogonal to the center axis $X_o$ is at its maximum; in the state illustrated in FIG. 7(B), with the almost all of the fluid 280 having been discharged out of the cavities of the deformable sections 220, the thickness h of the bowtie filter 200 is at its minimum. In this manner, as the sectional shape of the X-ray absorbing portion (the fixed section 210 and the movable sections 230) of the bowtie filter 200 varies and the thickness on the center axis $X_o$ varies in the x direction, it is made possible to vary the quantity of X-rays penetrating the X-ray absorbing portion of the bowtie filter 200.

In this way, the sectional shape of the X-ray absorbing portion of the bowtie filter 200 is varied by tilting the movable axes 240 with the movable means 270.

Preferably, the X-ray absorbing portion of one bowtie filter 200 can be continuously varied into many different shapes by tilting the movable axes 240 with the movable means 270.

The thickness (or height or depth) of the bowtie filter 200 in the x direction is determined by the following equation.

$$h(x, \theta) = h0 + h1(x) + h2(x, \theta) + h3(x, \theta) \qquad (1)$$

Sign h0 represents the thickness of the base portion 211 of the fixed section 210, and its value is constant independent of the position in the x direction.

Sign h1(x) represents the thickness of the inclined portions 212 of the fixed section 210 in the x direction and, since the angle of inclination a of the inclined portions 212 relative to the flat face of the base portion 211 is known, the thickness h1(x) of the inclined portions 212 can be calculated according to the position in the x direction.

Sign h2(x, $\theta$) represents the thickness of the deformable sections 220 in the x direction, which is the thickness along the center axis $X_o$ when the volumes of the cavities of the deformable sections 220 have varied according to the angle $\theta$ by which the movable axes 240 have been tilted with the movable means 270. The value of h2(x, $\theta$) can be calculated from the tilting angle $\theta$ and the position x in the x direction of the movable axes 240.

Sign h3(x, θ) represents the thickness of the movable sections 230 in the x direction, which is the thickness along the center axis $X_o$ reflecting the inclination of the movable sections 230 according to the angle θ by which the movable axes 240 have been tilted with the movable means 270. The value of this h3 (x, θ) can be calculated from the tilting angle θ and the position x in the x direction of the movable axes 240.

The values of h1(x), h2(x, θ) and h3(x, θ) are calculated in advance, applied to Equation 1 and, by using the tilting angle θ and the position x in the x direction as parameters, can be stored in a memory with the heights (depths) of the bowtie filter 200 being tabulated. Alternatively, a thickness corresponding to the tilting angle θ can be calculated on each individual occasion by using a computer.

To obtain the desired shape of the bowtie filter 200 by using the aforementioned tabulated values stored in the memory or referencing the individually calculated results, by having a computer to perform processing for instance, it can be known how much the movable axes 240 should be tilted with the movable means 270.

Bowtie Filter Control Section

In order to automatically perform shape control of the X-ray absorbing portion configured of the fixed section 210 and the movable sections 230 of such a bowtie filter 200, the bowtie filter control section 40 is added to the scanning gantry 2 described with reference to FIG. 1. The bowtie filter control section 40 is illustrated in FIG. 3.

The bowtie filter control section 40, configured of a memory and a computer for instance, stores in the memory the aforementioned thicknesses h of the bowtie filter 200 in the x direction, calculated in advance, in a tabulated form by using the tilting angle θ and the position x in the x direction as parameters. The bowtie filter control section 40 reversely derives from the memory the tilting angle θ for shaping the bowtie filter 200 in a desired way, and drives the movable means 270 on the basis of the derived result. In this case, of course, the movable means 270 has a motor capable of control for,tilting the movable axes 240, and the bowtie filter control section 40 tilts the movable axes 240 by a required tilting angle via the movable means 270.

Incidentally, the bowtie filter control section 40 represents control means for an X-ray distribution adjusting filter apparatus one mode of implementing the present invention.

By using the bowtie filter 200 in the second mode of implementing the invention, it is possible to provide a bowtie filter (X-ray distribution adjusting filter apparatus) whose X-ray absorbing portion can be continuously varied in shape either automatically or manually.

Also, as the shape of the X-ray absorbing portion of the bowtie filter can be freely and continuously varied by using such a bowtie filter (X-ray distribution adjusting filter apparatus) and further using the bowtie filter control section 40 according to the type of the subject and the region to be examined of the subject, it is possible to adjust the X-ray intensity distribution as desired. As a result, more accurate imaging results can be obtained, and reconstructed images of higher grade can be provided.

To add, such a bowtie filter 200 can also be applied to the processing of beam hardening using a phantom and the like.

Although the right and left movable sections 230 in the bowtie filter 200 in the second mode of implementation described above are tilted by the same tilting angle by way of example, it also possible to vary the tilting angles of the right and left movable sections 230. Or it is also possible to differentiate the curvatures of the curved faces 232 of the right and left movable sections 230.

Further, it is possible to differentiate the inclination angles of the right and left inclined portions 212 of the fixed section 210.

Thus, in order to realize a shape and shape variation as desired for the X-ray absorbing portion, the fixed section 210 and the movable sections 230 of desired shapes are prepared to enable the movable sections 230 to be tilted so as to realize the desired shape.

To compare the bowtie filter in the second mode of implementation and the bowtie filter in the first mode of implementation, the second mode of implementation has such advantages that only one bowtie filter suffices and the X-ray absorbing portion can be continuously varied in shape.

Third Mode of Implementation

A bowtie filter as the X-ray distribution adjusting filter apparatus in a third mode of implementing the present invention will be described with reference to FIG. 8 and FIG. 9.

FIG. 8(A) shows a sectional view of the bowtie filter in the third mode of implementation, and FIG. 8(B), a profile of the bowtie filter illustrated in FIG. 8(A).

A bowtie filter 300 in the third mode of implementation has a basic bowtie filter 310 having a flat face 312 and a curved inner wall 311, a first removable bowtie filter 330 having a curved outer wall 331 and a curved inner wall 332, a second removable bowtie filter 340 having a curved outer wall 341 and a curved inner wall 342, an inner guide member 350 having a curved outer wall 351 and a flat and thick bottom guide member 320.

The basic bowtie filter 310 corresponds to the basic X-ray distribution adjusting filter portion according to the invention, the first removable bowtie filter 330 corresponds to the removable X-ray distribution adjusting filter portion according to the invention, and the second removable bowtie filter 340 corresponds to the second removable X-ray distribution adjusting filter portion according to the invention.

The basic bowtie filter 310, the first removable bowtie filter 330 and the second removable bowtie filter 340 substantially constitute the X-ray absorbing portion.

Although the bottom guide member 320 and the inner guide member 350 are not indispensable requirements as a matter of principle, they are provided to stably and smoothly realize the insertion and removal of the first removable bowtie filter 330 and the second removable bowtie filter 340.

In the bottom guide member 320 are formed guide grooves to enable the first removable bowtie filter 330 and the second removable bowtie filter 340 to slide in the direction of orthogonally crossing the sheet of FIG. 8(A).

The inner guide member 350, positioned within the basic bowtie filter 310, is arranged so as to stably and smoothly realize the insertion and removal of the first removable bowtie filter 330 and the second removable bowtie filter 340 between it and the basic bowtie filter 310.

The bottom guide member 320 and the inner guide member 350 are formed of a material having a low X-ray absorption characteristic, such as a foamed material. Thus, since it is preferable for the bottom guide member 320 and the inner guide member 350 to be minimal in X-ray absorption, they are formed of a material having a low X-ray absorption characteristic.

The curved inner wall 311 of the basic bowtie filter 310 has a shape substantially identical with the curved outer wall 331 of the first removable bowtie filter 330.

The curved inner wall 332 of the first removable bowtie filter 330 has a shape substantially identical with the curved outer wall 341 of the second removable bowtie filter 340.

The curved inner wall 342 of the second removable bowtie filter 340 has a shape substantially identical with the curved outer wall 351 of the inner guide member 350.

The basic bowtie filter 310, the first removable bowtie filter 330 and the second removable bowtie filter 340 are all formed of an appropriate X-ray absorptive as filters, like the materials of the bowtie filter in the first and second modes of implementation.

Figure 9A:
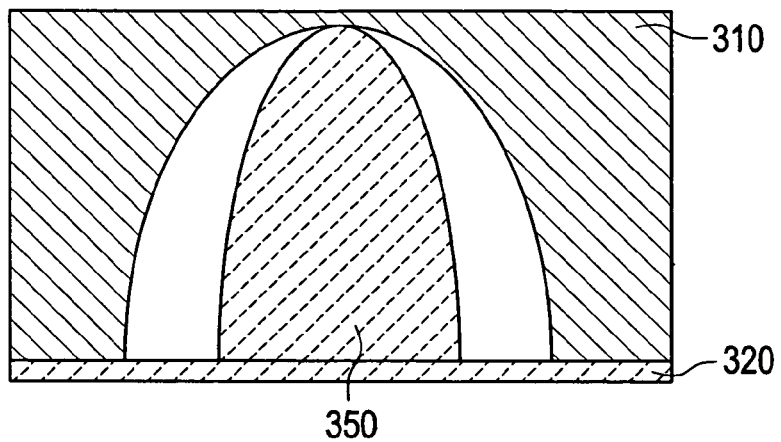
FIGS. 9(A) through 9(C) illustrate the states of combination of the bowtie filter illustrated in FIGS. 8(A) and 8(B).

FIG. 9(A) shows a state in which the first removable bowtie filter 330 and the second removable bowtie filter 340 are not inserted between the basic bowtie filter 310 and the inner guide member 350.

This is a state in which the first removable bowtie filter 330 and the second removable bowtie filter 340 are taken out of the basic bowtie filter 310 and the space defined by the basic bowtie filter 310 and the inner guide member 350 by using a shaft 335 connected to the first removable bowtie filter 330 and a shaft 345 connected to the second removable bowtie filter 340. This state represents a first basic distribution adjustment characteristic defined by the basic bowtie filter 310 alone.

Figure 9B:
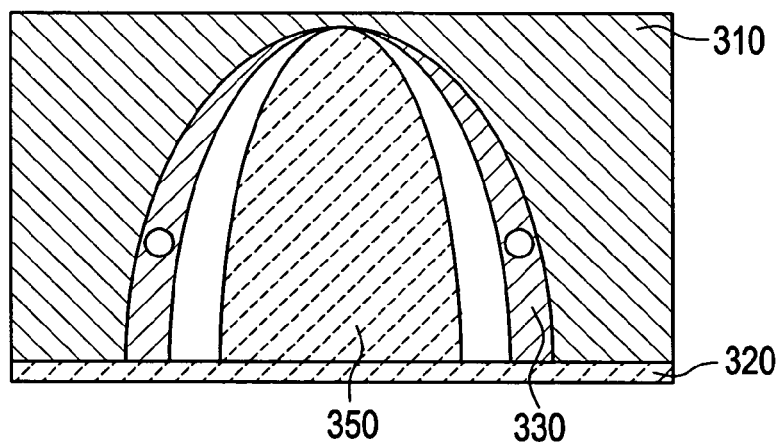

FIG. 9(B) shows a sectional view of a state in which the first removable bowtie filter 330 is inserted between the basic bowtie filter 310 and the inner guide member 350.

By moving the shaft 335 connected to the first removable bowtie filter 330 in the direction of an arrow illustrated in FIG. 8(B), the first removable bowtie filter 330 can be accommodated along the curved inner wall 311 of the basic bowtie filter 310 between the curved inner wall 311 of the basic bowtie filter 310 and the curved outer wall 351 of the inner guide member 350.

As the shape of the curved inner wall 311 and that of the curved outer wall 331 are identical, when the first removable bowtie filter 330 is accommodated within the basic bowtie filter 310, it results in a state in which the basic bowtie filter 310 and the first removable bowtie filter 330 are configured in a substantially integrated state.

This causes the bowtie filter 300 to manifest a second distribution adjustment characteristic defined by the basic bowtie filter 310 and the first removable bowtie filter 330 combined in an integrated way.

Figure 9C:
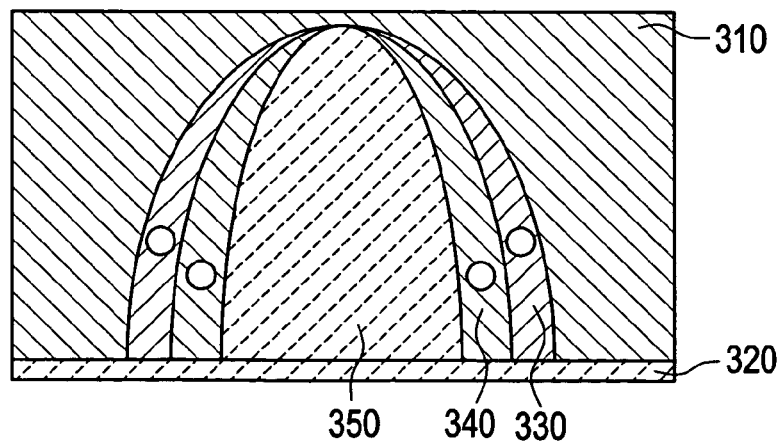

FIG. 9(C) shows a sectional view of a state in which the first removable bowtie filter 330 and the second removable bowtie filter 340 are inserted between the basic bowtie filter 310 and the inner guide member 350.

By moving the shaft 345 connected to the second removable bowtie filter 340 in the direction of an arrow shown in FIG. 8(B), the second removable bowtie filter 340 can be accommodated along the curved inner wall 332 of the first removable bowtie filter 330 between the curved inner wall 332 of the first removable bowtie filter 330 and the curved outer wall 351 of the inner guide member 350.

As the shape of the curved inner wall 332 and that of the curved outer wall 351 are identical, when the second removable bowtie filter 340 is accommodated within the space between the first removable bowtie filter 330 and the inner guide member 350, it results in a state in which the basic bowtie filter 310, the first removable bowtie filter 330 and the second removable bowtie filter 340 are configured in a substantially integrated state.

This causes the bowtie filter 300 to manifest a third distribution adjustment characteristic defined by the basic bowtie filter 310, the first removable bowtie filter 330 and the second removable bowtie filter 340 combined in an integrated way.

As described above, the bowtie filter 300 of the X-ray distribution adjusting filter apparatus in the third mode of implementing the invention, the bowtie filter 300 manifesting a plurality of intensity distribution adjustment characteristics can be varied by appropriately inserting the first removable bowtie filter 330 and the second removable bowtie filter 340 inside the basic bowtie filter 310 or removing therefrom.

If drive means for driving the shaft 335 and the shaft 345, for instance drive means which has a motor and a screw and whose screw turns as the motor revolves to cause, via the shaft 335 and/or the shaft 345, the first removable bowtie filter 330 the second removable bowtie filter 340 to slide is connected and the first removable bowtie filter 330 and the second removable bowtie filter 340 are inserted or removed by using the drive means and the bowtie filter control section 40, it is made possible to configure a bowtie filter 300 having a desired shape automatically, for instance according to the region of the subject 50 to be imaged and to obtain a desired X-ray intensity distribution characteristic.

As a result, in the X-ray CT apparatus described with reference to FIG. 1 through FIG. 3, it is made possible to obtain picked-up images of the subject 50 or the phantom.

Fourth Mode of Implementation

Figure 10A:
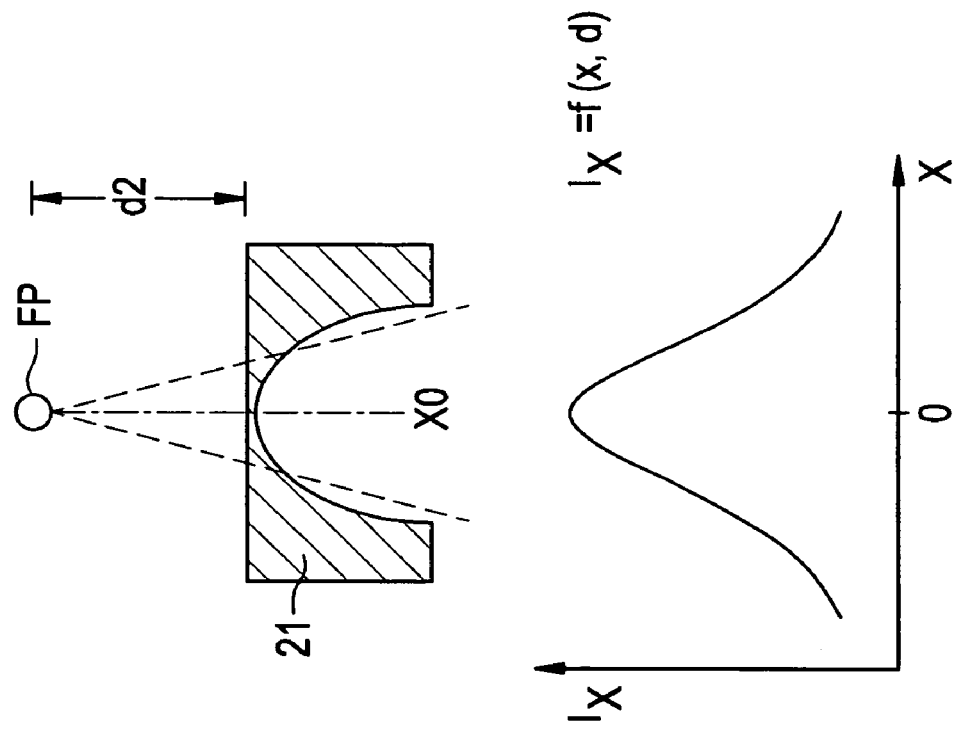
FIGS. 10(A) and 10(B) illustrates the method of X-ray intensity distribution adjustment by a bowtie filter in a fourth mode of implementing the invention.
Figure 10B:
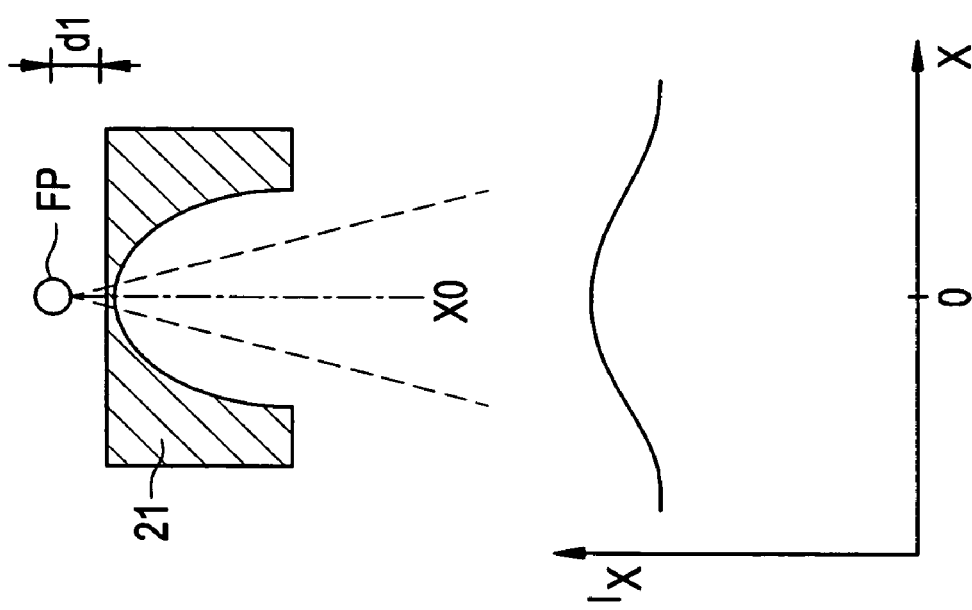

A bowtie filter as the X-ray distribution adjusting filter apparatus in a fourth mode of implementing the present invention will be described with reference to FIGS. 10 and FIG. 11. FIGS. 10(A) and 10(B) illustrate a case in which the bowtie filter 21 is moved along the center axis $X_o$ relative to the focal position FP of the X-ray tube 20 and the X-ray distribution in that case.

Since X-rays emitted from the X-ray tube 20 diffuse toward the X-ray detector 24 in a fan shape, the quantity absorbed when penetrating the bowtie filter 21 varies with the position of the bowtie filter 21 along the center axis $X_o$, depending on the shape and the position of the bowtie filter 21. Therefore, even if a bowtie filter 21 of the same sectional shape is used, the distribution of X-ray intensity Ix can be varied as illustrated in FIGS. 10(A) and 10(B) by varying the position of the bowtie filter 21 relative to the focal position of the X-ray tube 20 from d1 to d2.

Figure 11:
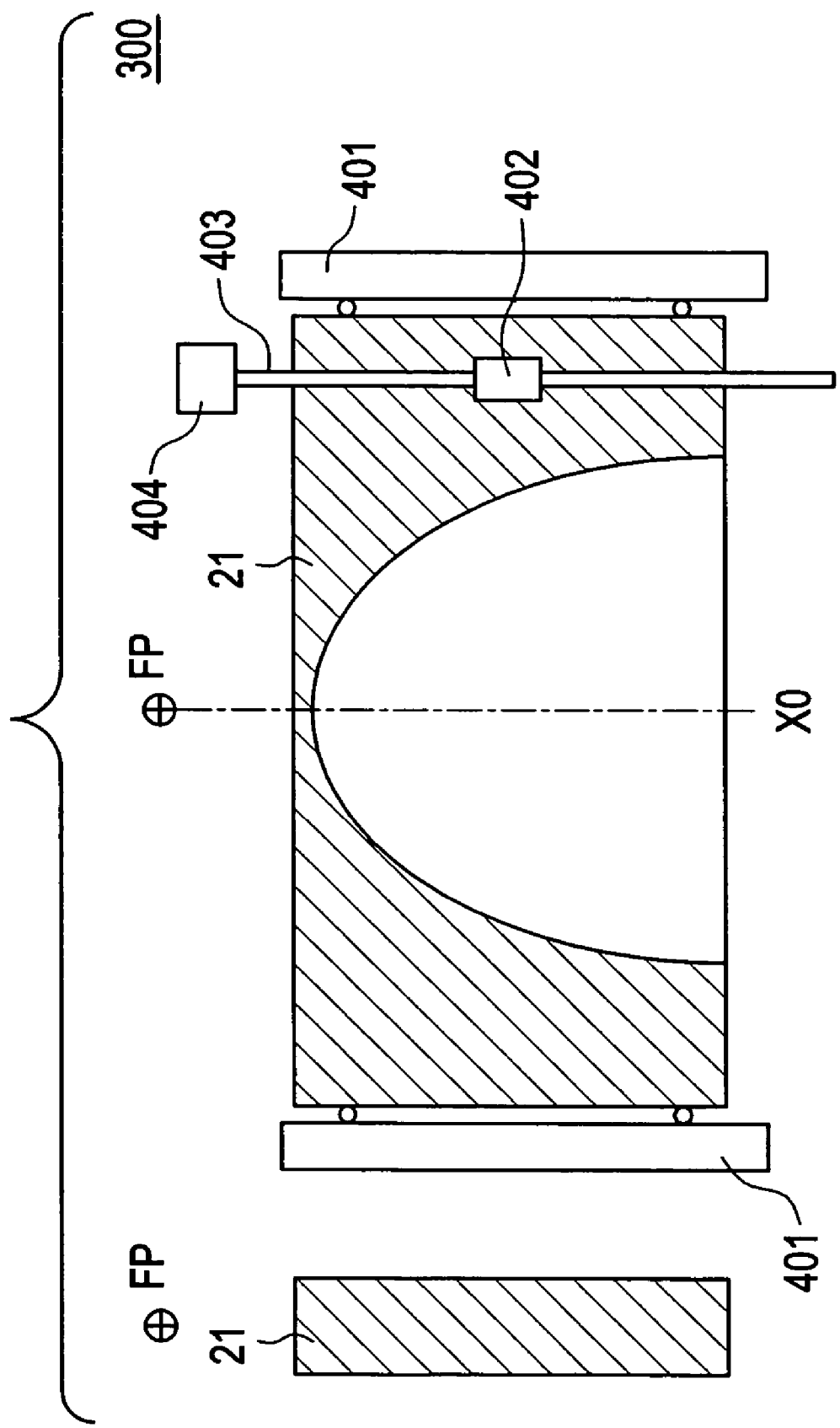
FIG. 11 is a diagram illustrating one specific example of X-ray intensity distribution adjustment method for the bowtie filter in the fourth mode of implementing the invention illustrated in FIGS. 10(A) and 10(B).

FIG. 11 illustrates one specific example of method of moving the bowtie filter 21 along its center axis $X_o$ on the basis of the findings described above.

The bowtie filter 21 is fitted to be vertically slidable along two guide members 401 provided on both sides.

A nut 402 is embedded in the bowtie filter 21, and a rotary screw 403 is fitted, engaged with this nut 402. To an end of the rotary screw 403 is connected a motor 404 for turning the rotary screw 402.

The motor 404 is turned by, for instance, the bowtie filter control section 40. The turning of the motor 404 can move the bowtie filter 21 up and down along the two guide members 401 via the nut 402 with which the rotary screw 403 is engaged in rotation. As a result, the bowtie filter 21 can be moved by a desired distance relative to the focal position FP of the X-ray tube 20 as illustrated in FIGS. 10(A) and 10(B).

The guide members 401, the nut 402, the rotary screw 403 and the motor 404 will be referred to as moving means for the bowtie filter 21, and the bowtie filter control section 40, as movement control means.

If the bowtie filter 21 and drive means illustrated in FIG. 11 is applied to the X-ray CT apparatus described with reference to FIG. 1 through FIG. 3, picked-up images of high precision can be obtained.

To add, in the fourth mode of implementation, it is also possible to use neither the motor 404 nor the bowtie filter control section 40, but to obtain a similar X-ray intensity distribution to what was described above by manually turning X-ray intensity distribution to what was described above by manually turning the rotary screw 403.

Fifth Mode of Implementation

As the bowtie filter 21 to used in the fourth mode of implementation, a bowtie filter 100, 200 or 300 described as second or third mode of implementation can be used instead of the above-described bowtie filter having a fixed curved shape.

Since the bowtie filter 100, the bowtie filter 200 or the bowtie filter 300 in itself can adjust the X-ray transmission characteristic, combination of this X-ray transmission characteristic variation and the positional adjustment of the bowtie filter makes it possible to vary the X-ray transmission characteristic or the X-ray distribution adjustment characteristic as desired.

Although such an adjustment method is complex, using the bowtie filter control section 40 would make it easy. Thus, the characteristics of the bowtie filter and the characteristics resulting from the positional variation of that bowtie filter are measured in advance, and the results of measurement are stored into the memory of the bowtie filter control section 40.

When the subject 50 or a phantom is to be actually imaged, the data stored in the memory of the bowtie filter control section 40 are referenced and, while the bowtie filter control section 40 adjusts the shape and characteristics of the bowtie filter, the position of the bowtie filter is adjusted.

The implementation of the X-ray distribution adjusting filter apparatus (bowtie filter) and the X-ray CT apparatus according to the present invention is not limited to the examples of mode of implementation described and illustrated above, but it can take on various modifications within the technical scope of the invention.

The invention claimed is:

1. An X-ray distribution adjusting filter apparatus for adjusting a distribution of penetration intensity of X-rays emitted from an X-ray source and expanding in a predetermined shape outward from center axis of the X-rays, said X-ray distribution adjusting filter apparatus comprising:
   a curved face having a predetermined curvature along said center axis;
   an X-ray absorbing portion formed of an X-ray absorbing material, wherein said distribution of the penetration intensity of X-rays is adjusted by varying a shape of said X-ray absorbing portion of the X-ray distribution adjusting filter apparatus;
   a fixed section including a base portion uniform in thickness along said center axis, and inclined portions linked to or formed integrally with the base portion, symmetrically formed about said center axis and on both sides of said center axis, and each having an inclined face with a predetermined inclination relative to a flat face of said base portion;
   first and second movable sections formed on both sides of said center axis, each configured to pass said center axis and to be tiltable on a plane orthogonal to said center axis, pivoting on a center point, which is the position where one-side ends of said inclined faces of said fixed section are coupled, and having a flat face positioned on the side opposite to said inclined faces of said fixed section and a curved face opposite to the flat face; and
   first and second deformable sections having opposite ends each opposite to said coupling position of each of said inclined faces of said fixed section, and expansible means disposed between the ends of said flat faces of said first and second movable sections, opposite to the opposite ends, and expanding or contracting according to the pivoting of said first and second movable sections, in which cavities defined by said inclined faces of said fixed section, said flat faces of said movable sections and said expansible means are filled with fluid to keep the insides of said cavities in a filled state, wherein said fixed section and said movable sections are formed of an X-ray absorbing material to constitute said X-ray absorbing portion.

2. The X-ray distribution adjusting filter apparatus according to claim 1, wherein said inclined faces of said fixed section and said flat faces of said movable sections are caused to approach or move away from each other by the tilting of said first and second movable sections pivoting on said center point to vary the quantities of said fluid in the cavities of said movable sections, and to vary the sectional shape of said X-ray absorbing portion of the X-ray distribution adjustment filter apparatus.

3. An X-ray distribution adjusting filter apparatus for adjusting a distribution of penetration intensity of X-rays emitted from an X-ray source and expanding in a predetermined shape outward from center axis of the X-rays, said X-ray distribution adjusting filter apparatus comprising:
   a curved face having a predetermined curvature along said center axis;
   an X-ray absorbing portion formed of an X-ray absorbing material, wherein said distribution of the penetration intensity of X-rays is adjusted by varying a shape of said X-ray absorbing portion of the X-ray distribution adjusting filter apparatus,
   a basic X-ray distribution adjusting filter portion symmetrically shaped about said center axis and having a curved inner wall; and
   a removable X-ray distribution adjusting filter portion symmetrically shaped about said center axis and having a first curved outer wall whose shape is identical with the shape of said curved inner wall of said basic X-ray distribution adjusting filter portion and a first curved inner wall on a face opposite to the first curved outer wall, capable of being inserted to or discharged from an inside of said basic X-ray distribution adjusting filter portion, with said first curved outer wall being run along said curved inner wall of said basic X-ray distribution adjusting filter portion, wherein:
   said basic X-ray distribution adjusting filter portion and said removable X-ray distribution adjusting filter portion are formed of a material that can absorb X-rays, and
   the insertion or removal of said removable X-ray distribution adjusting filter portion into or from said basic X-ray distribution adjusting filter portion causes the sectional shape of said X-ray absorbing portion of the X-ray distribution adjusting filter apparatus to vary.

4. The X-ray distribution adjusting filter apparatus according to claim 3, further including:
   a second removable X-ray distribution adjusting filter portion symmetrically shaped about said center axis and having a second curved outer wall whose shape is identical with the shape of said first curved inner wall of said removable X-ray distribution adjusting filter portion and a second curved inner wall on a face opposite to the second curved outer wall, capable of being inserted to or discharged from an inside of said removable X-ray distribution adjusting filter portion, with said second curved outer wall being run along said first curved inner wall of said removable X-ray distribution adjusting filter portion, wherein:

said second removable X-ray distribution adjusting filter portion is formed of a material that can absorb X-rays, and the insertion or removal of said removable X-ray distribution adjusting filter portion and said second removable X-ray distribution adjusting filter portion causes the sectional shape of said X-ray absorbing portion of the X-ray distribution adjusting filter apparatus.

5. The X-ray distribution adjusting filter apparatus according to claim 4, wherein:

within said basic X-ray distribution adjusting filter portion, an inner guide member is arranged which is formed of a member which absorbs less of said X-rays and whose curved outer wall is identical in shape with said curved inner wall of said removable X-ray distribution adjusting filter portion or said curved inner wall of said second removable X-ray distribution adjusting filter portion, and said removable X-ray distribution adjusting filter portion and/or said second removable X-ray distribution adjusting filter portion are inserted into or removed from a space between said basic X-ray distribution adjusting filter portion and said inner guide member with said inner guide member as guiding means.

6. An X-ray CT apparatus comprising:

an X-ray source;

X-ray detecting section; and an X-ray distribution adjusting filter apparatus configured to adjust the distribution of the penetration intensity of X-rays emitted from said X-ray source and configured to disperse in a predetermined shape from the center axis of the X-rays linking the focal position of said X-ray source and the center of said X-ray detecting section on a plane orthogonal to said center axis, wherein said X-ray distribution adjusting filter apparatus comprises:

a curved face along said center axis;

an X-ray absorbing portion formed of an X-ray absorbing material, in which the distribution of the penetration intensity of said X-rays can be adjusted by varying the sectional shape of said X-ray absorbing portion of the X-ray distribution adjusting filter apparatus;

a fixed section including a base portion uniform in thickness along said center axis, and inclined portions linked to or formed integrally with the base portion, symmetrically formed about said center axis and on both sides of said center axis, and each having an inclined face with a predetermined inclination relative to a flat face of said base portion;

first and second movable sections formed on both sides of said center axis, each configured to pass said center axis and to be tiltable on a plane orthogonal to said center axis, pivoting on a center point, which is the position where one-side ends of said inclined faces of said fixed section are coupled, and having a flat face positioned on the side opposite to said inclined faces of said fixed section and a curved face opposite to the flat face; and first and second deformable sections having opposite ends each opposite to said coupling position of each of said inclined faces of said fixed section, and an expansible section disposed between the ends of said flat faces of said first and second movable sections, opposite to the opposite ends, and expanding or contracting according to the pivoting of said first and second movable sections, in which cavities defined by said inclined faces of said fixed section, said flat faces of said movable sections and said expansible section are filled with fluid to keep the insides of said cavities in a filled state, wherein:

said fixed section and said movable sections are formed of an X-ray absorbing material to constitute said X-ray absorbing portion.

7. The X-ray CT apparatus according to claim 6, wherein said inclined faces of said fixed section and said flat faces of said movable sections are caused to approach or move away from each other by the tilting of said first and second movable sections pivoting on said center point to vary the quantities of said fluid in the cavities of said movable sections, and to vary the sectional shape of said X-ray absorbing portion of the X-ray distribution adjustment filter apparatus.

8. The X-ray CT apparatus according to claim 7, comprising:

a fluid accommodating section for pressing said fluid to said cavity so as to fill said cavities with said fluid without obstructing the rotation of said movable sections and in response to the rotation of said movable sections; and a movable device for rotating said movable sections.

9. The X-ray CT apparatus according to claim 8, wherein:

said movable sections are continuously tilted via said movable device to continuously vary the sectional shape of said X-ray absorbing portion of the X-ray distribution adjustment filter apparatus.

10. The X-ray CT apparatus according to claim 8, wherein:

said movable sections can be continuously tilted via said movable device to continuously vary the sectional shape of said X-ray absorbing portion of the X-ray distribution adjustment filter apparatus.

11. The X-ray CT apparatus according to claim 7, further including an X-ray distribution adjusting filter apparatus control section, in which the shape and characteristics of said X-ray absorbing portion of said X-ray distribution adjusting filter apparatus are found on each individual occasion according to the tilted position of said movable sections, or has memory section in which are stored said shape and characteristics figured out in advance, and said found results or the results stored in said memory section are referenced to tilt said movable sections according to the desired shape and characteristics of the X-ray absorbing portion of said X-ray distribution adjusting filter apparatus.

12. An X-ray CT apparatus comprising:

an X-ray source;

X-ray detecting section; and an X-ray distribution adjusting filter apparatus configured to adjust a distribution of a penetration intensity of X-rays emitted from said X-ray source and configured to disperse in a predetermined shape from a center axis of the X-rays linking a focal position of said X-ray source and a center of said X-ray detecting section on a plane orthogonal to said center axis, said X-ray distribution adjusting filter apparatus comprising:

a curved face along said center axis;

an X-ray absorbing portion formed of an X-ray absorbing material, in which the distribution of the penetration intensity of said X-rays can be adjusted by varying the sectional shape of said X-ray absorbing portion of the X-ray distribution adjusting filter apparatus;

a basic X-ray distribution adjusting filter portion symmetrically shaped about said center axis and having a curved inner wall; and a removable X-ray distribution adjusting filter portion symmetrically shaped about said center axis and having a first curved outer wall whose shape is identical with the shape of said curved inner wall of said basic X-ray distribution adjusting filter portion and a first curved inner wall on a face opposite to the first curved outer wall, capable of being inserted to or discharged from an inside of said basic X-ray distribution adjusting filter portion, with said first curved outer wall being run along said curved inner wall of said basic X-ray distribution adjusting filter portion, wherein:

said basic X-ray distribution adjusting filter portion and said removable X-ray distribution adjusting filter portion are formed of a material that can absorb X-rays, and the insertion or removal of said removable X-ray distribution adjusting filter portion into or from said basic X-ray distribution adjusting filter portion causes the sectional shape of said X-ray absorbing portion of the X-ray distribution adjusting filter apparatus to vary.

13. The X-ray CT apparatus according to claim 12, in which said X-ray distribution adjusting filter apparatus further includes:

a second removable X-ray distribution adjusting filter portion symmetrically shaped about said center axis and having a second curved outer wall whose shape is identical with the shape of said first curved inner wall of said removable X-ray distribution adjusting filter portion and a second curved inner wall on a face opposite to the second curved outer wall, capable of being inserted to or discharged from an inside of said removable X-ray distribution adjusting filter portion, with said second curved outer wall being run along said first curved inner wall of said removable X-ray distribution adjusting filter portion, wherein:

said second removable X-ray distribution adjusting filter portion is formed of a material that can absorb X-rays, and the insertion or removal of said removable X-ray distribution adjusting filter portion and said second removable X-ray distribution adjusting filter portion causes the sectional shape of said X-ray absorbing portion of the X-ray distribution adjusting filter apparatus.

14. The X-ray CT apparatus according to claim 13, wherein:

said X-ray distribution adjustment filter apparatus includes, within said basic X-ray distribution adjusting filter portion, an inner guide member arranged, which is formed of a member which absorbs less of said X-rays and whose curved outer wall is identical in shape with said curved inner wall of said removable X-ray distribution adjusting filter portion or said curved inner wall of said second removable X-ray distribution adjusting filter portion, and said removable X-ray distribution adjusting filter portion and/or said second removable X-ray distribution adjusting filter portion are inserted into or removed from a space between said basic X-ray distribution adjusting filter portion and said inner guide member with said inner guide member as guiding means.

15. The X-ray CT apparatus according to claim 12, further including:

an X-ray distribution adjusting filter apparatus control section which has memory section in which the shape and characteristics of said X-ray absorbing portion of the X-ray distribution adjusting filter apparatus when using said one or a plurality of removable X-ray distribution adjusting filter portions in combination are found in advance and stored, and which inserts or removes said one or a plurality of removable X-ray distribution adjusting filter portions according to the desired shape and characteristics of said X-ray absorbing portion with reference to the results stored in said memory section.

16. An X-ray CT apparatus including:

an X-ray source;

X-ray detecting section;

an X-ray distribution adjusting filter apparatus having, in order to adjust the distribution of the penetration intensity of X-rays emitted from said X-ray source and dispersing in a predetermined shape from the center axis of the X-rays linking the focal position of said X-ray source and the center of said X-ray detecting section on a plane orthogonal to said center axis, a curved face along said center axis, and including an X-ray absorbing portion formed of an X-ray absorbing material; and an X-ray distribution adjusting filter apparatus control section for adjusting the distribution of the penetration intensity of X-rays penetrating said X-ray absorbing portion by varying the position of said X-ray absorbing portion of said X-ray distribution adjusting filter apparatus relative to the focal position of said X-ray source, said X-ray distribution adjusting filter apparatus comprising:

a fixed section including a base portion uniform in thickness along said center axis, and inclined portions linked to or formed integrally with the base portion, symmetrically formed about said center axis and on both sides of said center axis, and each having an inclined face with a predetermined inclination relative to a flat face of said base portion;

first and second movable sections formed on both sides of said center axis, each configured to pass said center axis and to be tiltable on a plane orthogonal to said center axis, pivoting on a center point, which is the position where one-side ends of said inclined faces of said fixed section are coupled, and having a flat face positioned on the side opposite to said inclined faces of said fixed section and a curved face opposite to the flat face; and first and second deformable sections having opposite ends each opposite to said coupling position of each of said inclined faces of said fixed section, and expansible section disposed between the ends of said flat faces of said first and second movable sections, opposite to the opposite ends, and expanding or contracting according to the pivoting of said first and second movable sections, in which cavities defined by said inclined faces of said fixed section, said flat faces of said movable sections and said expansible section are filled with fluid to keep the insides of said cavities in a filled state, wherein:

said fixed section and said movable sections are formed of an X-ray absorbing material to constitute said X-ray absorbing portion.

17. The X-ray CT apparatus according to claim 16, wherein said inclined faces of said fixed section and said flat faces of said movable sections are caused to approach or move away from each other by the tilting of said first and second movable sections pivoting on said center point to vary the quantities of said fluid in the cavities of said movable sections, and to vary the sectional shape of said X-ray absorbing portion of the X-ray distribution adjustment filter apparatus.

18. An X-ray CT apparatus comprising:
an X-ray source;
X-ray detecting section;
an X-ray distribution adjusting filter apparatus configured to adjust a distribution of a penetration intensity of X-rays emitted from said X-ray source and configured to disperse in a predetermined shape from a center axis of the X-rays linking a focal position of said X-ray source and a center of said X-ray detecting section on a plane orthogonal to said center axis, said X-ray distribution adjusting filter apparatus comprising:
a curved face along said center axis;
an X-ray absorbing portion formed of an X-ray absorbing material;
a basic X-ray distribution adjusting filter portion symmetrically shaped about said center axis and having a curved inner wall; and
a removable X-ray distribution adjusting filter portion symmetrically shaped about said center axis and having a first curved outer wall whose shape is identical with the shape of said curved inner wall of said basic X-ray distribution adjusting filter portion and a first curved inner wall on a face opposite to the first curved outer wall, capable of being inserted to or discharged from an inside of said basic X-ray distribution adjusting filter portion, with said first curved outer wall being run along said curved inner wall of said basic X-ray distribution adjusting filter portion, wherein:
said basic X-ray distribution adjusting filter portion and said removable X-ray distribution adjusting filter portion are formed of a material that can absorb X-rays, and
the insertion or removal of said removable X-ray distribution adjusting filter portion into or from said basic X-ray distribution adjusting filter portion causes the sectional shape of said X-ray absorbing portion of the X-ray distribution adjusting filter apparatus to vary; and
an X-ray distribution adjusting filter apparatus control section for adjusting the distribution of the penetration intensity of X-rays penetrating said X-ray absorbing portion by varying the position of said X-ray absorbing portion of said X-ray distribution adjusting filter apparatus relative to the focal position of said X-ray source.

* * * * *